United States Patent [19]

Baur et al.

[11] Patent Number: 4,681,946
[45] Date of Patent: Jul. 21, 1987

[54] PREPARATION OF NICOTINAMIDE

[75] Inventors: Karl G. Baur, Ludwigshafen; Volker Diehl, Ellerstadt; Peter Stops, Altrip; Hans Hellbach, Lampertheim; Erwin Brunner, Ludwigshafen, all of Fed. Rep. of Germany

[73] Assignee: BASF Aktiengesellschaft, Ludwigshafen, Fed. Rep. of Germany

[21] Appl. No.: 797,990

[22] Filed: Nov. 14, 1985

Related U.S. Application Data

[63] Continuation of Ser. No. 555,402, Nov. 28, 1983, abandoned.

[30] Foreign Application Priority Data

Dec. 2, 1982 [DE] Fed. Rep. of Germany ....... 3244522

[51] Int. Cl.$^4$ ..................... C07B 43/06; C07D 213/82
[52] U.S. Cl. ................................... 546/317
[58] Field of Search ........................ 546/317

[56] References Cited

U.S. PATENT DOCUMENTS

| 2,412,749 | 12/1946 | Pike et al. | 546/317 |
| 2,916,494 | 12/1959 | O'Brochta | 546/319 |
| 4,327,219 | 4/1982 | Gelbein | 546/317 |

OTHER PUBLICATIONS

Pratt, H. R. C. "Countercurrent Separation Processes" pp. 191–209 (1967) Elsevier Publishing Co.
Karger, B. L. et al. "An Introduction to Separation Science" pp. 181–210 Wiley & Sons, New York (1973).
CRC Handbook of Chemistry and Physics, 62nd Ed. (1981) p. C.-398.
Hammond, "Separation and Purification of Materials" New York Philosophical Library (1958) pp. 19–22.

Primary Examiner—John M. Ford
Assistant Examiner—Dale A. Bjorkman
Attorney, Agent, or Firm—John H. Shurtleff

[57] ABSTRACT

A process for the preparation of nicotinamide by amidation of a nicotinic acid/nicotinamide melt, vacuum distillation of the amidation mixture, removal of the nicotinamide as the bottom product and recycling of the top product, depleted with respect to nicotinamide, into the amidation stage together with addition of fresh amounts of nicotinic acid.

7 Claims, 1 Drawing Figure

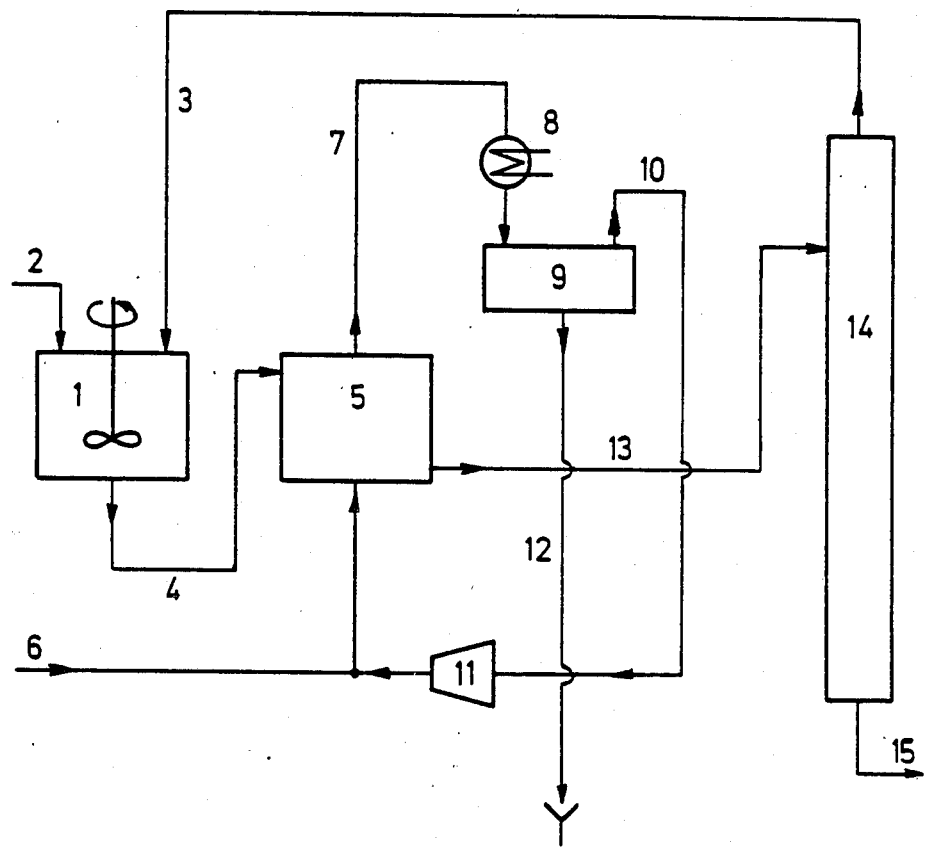

PREPARATION OF NICOTINAMIDE

This application is a continuation, of application Ser. No. 555,402, filed Nov. 28, 1983 abandoned.

The present invention relates to an improved process for the preparation of nicotinamide, also called vitamin PP or niacinamide, by amidation of a nicotinic acid/nicotinamide melt predominantly containing nicotinic acid.

U.S. Pat. No. 2,412,749 discloses the preparation of nicotinamide by reacting nicotinic acid with gaseous ammonia at elevated temperatures, the water of reaction being removed by distillation. This process is unsatisfactory because the yield is only 60% of theory and a multistage crystallization is required to purify the nicotinamide, so that the yield of pure amide is even lower.

BRIEF DESCRIPTION OF DRAWING

The sole FIGURE shows a schematic drawing of the overall continuous process according to the invention.

It is an object of the present invention to propose an improved process for the preparation of nicotinamide, in which the amidation reaction proceeds with a better yield and no crystallization is required.

We have found that this object is achieved by reaction of a melt of nicotinic acid and nicotinamide with ammonia and vacuum distillation of the resulting amidation mixture.

In fact, we have found that, suprisingly, good yields of particularly pure nicotinamide are obtained in a simple manner by a process wherein a solution of nicotinic acid in nicotinamide is reacted in a first stage with an excess of ammonia at from 190° to 240° C., the water of reaction being removed at the same time by distillation, the resulting solution of nicotinic acid and, predominantly, nicotinamide is subjected, in a second stage, to vacuum distillation in which pure nicotinamide is removed at the bottom of the column and a mixture of nicotinic acid and nicotinamide with a lower nicotinamide content than the feed is removed at the top of the column, and the nicotinic acid/nicotinamide mixture obtained in the second stage is recycled to the first stage and replenished with fresh nicotinic acid.

The reaction in the first stage is carried out under atmospheric pressure or under a superatmospheric pressure of not more than about 60 bar, at from 190° to 240° C., usually from 200° to 220° C.

The ammonia is advantageously used in a molar excess, based on the nicotinic acid employed, of, for example, from 0.5 to 4, in particular from 1 to 2.5, times the molar amount required for the conversion.

If the amidation is carried out under atmospheric pressure, a conversion of as much as 85% is obtained with residence times of several hours, while a conversion of as much as 95% is obtained under superatmospheric pressure, e.g. from 2 to 60 bar.

Small amounts of pyridine and nicotinic acid nitrile are formed as by-products which have no further use, and are distilled off with the water of reaction.

The composition of the starting mixture of nicotinic acid and nicotinamide used for the amidation should be such that the mixture is completely liquid and homogeneous at the reaction temperature.

Mixtures with a higher nicotinic acid content, e.g. from 50 to 80% of nicotinic acid, are advantageously chosen. These mixtures have melting points of from 180° to 210° C. The temperature therefore does not have to reach or exceed the melting point of pure nicotinic acid, namely 236° C., at which decomposition of the nicotinic acid starts.

In principle, mixtures of nicotinic acid/nicotinamide in which the amide predominates could also be amidated if the top product from the 2nd stage, containing fresh nicotinic acid or recycled nicotinic acid, is added only at the rate at which amidation takes place. However, this provides hardly any advantage, since the reaction chamber must then be enlarged.

The amidation reaction can be carried out batchwise in a stirred kettle or autoclave or, preferably, continuously in a conventional arrangement, such as a stirred kettle cascade, bubble column, pressure tube or loop reactor cascade.

The composition of the crude mixture obtained in the amidation reaction varies, depending on the reaction parameters of pressure, residence time, temperature and excess of ammonia, and is, for example, from 60 to 95% by weight of nicotinamide, from 4 to 39% by weight of nicotinic acid, from 0.1 to 2% by weight of nicotinic acid nitrile and traces of pyridine, water and ammonia.

The second stage of the process according to the invention, i.e. distillation of the amidation mixture, has two aims: purification of the crude nicotinamide and recycling of unreacted nicotinic acid to the amidation stage. The distillation is carried out under certain general conditions. Although physical measurements show that nicotinic acid is a higher-boiling component than nicotinamide, corresponding to the vapor pressure curves of the pure compounds, the actual behavior of the nicotinic acid/nicotinamide mixture on distillation shows that a mixture containing not more than 50% by weight of nicotinic acid behaves like the more highly volatile component. It is therefore possible to concentrate the nicotinic acid at the top of the distillation column and to obtain pure nicotinamide as the bottom product.

Since nicotinamide decomposes above 190° C. as a function of the residence time and temperature, the distillation is advantageously carried out with substantially reduced pressure at the top of the column (2–10 mbar). Accordingly, there should be only a very small drop in pressure caused by the column and evaporator. A column packing which has an ordered hollow structure which repeats itself in all dimensions, vertical hollow channels inside the column packing being avoided and tight sealing being ensured between the structural elements and the column jacket, is therefore preferably used. Examples of suitable evaporators are thin film or falling film evaporators, negligible hold-up being required in the evaporation chamber, besides the low pressure loss.

Since the principal aim of the distillation stage according to the invention is depletion of the mixture in respect of nicotinic acid, the column should have a sufficient number of separation stages in the stripping section. In contrast, the rectifying section of the column is extremely small, in order to prevent the nicotinic acid becoming too highly concentrated at the top of the column. If this is not the case, the condensation temperature exceeds the melting point of the mixture at the top of the column.

The pure nicotinamide is removed at the bottom of the column, if necessary from a lateral take-off above the bottom.

Nicotinic acid is obtained at the top of the column, together with nicotinamide and the other lowboiling components, i.e. nicotinic acid nitrile and pyridine. It is not possible to obtain pure nicotinic acid at the top of the column, because of the azeotropy described above. The melting point of the azeotropic mixture, about 210° C., is above the boiling point of the mixture, so that it would be necessary to introduce a solvent at the top of the column. Since a solvent which is foreign to the system would have to be added to the feed mixture before introduction thereof into the column and would have to be removed again from the recycled stream after the distillation, nicotinamide is preferably used as the solvent in order to avoid this problem. The amount of nicotinamide can be controlled at the desired level, i.e. about 60% by weight, by the design of the rectifying section of the column and by adjustment of the column reflux ratio.

Furthermore, the concentration of low-boiling components, especially the presence of nicotinic acid nitrile, has an influence on the boiling/melting properties at the top of the column. Even small amounts of these highly volatile components greatly reduce the boiling point under constant pressure. On the other hand, the freezing point depression caused by these more highly volatile components is negligible. This means that the nicotinic acid nitrile concentration and the concentration of all the other low-boiling compounds, e.g. pyridine, water and ammonia, in the feed is advantageously kept extremely low.

The distillation and entire process are advantageously carried out continuously, the amidation and the distillation stage being linked. This is also illustrated in more detail with the aid of FIG. 1 and the Example which follows.

A mixing kettle 1 was fed with 110 kg/hour of fresh nicotinic acid via line 2 and 149 kg/hour, via line 3, of the nicotinic acid/nicotinamide mixture (weight ratio of 40:60) obtained as the top product in the distillation in column 14. The mixture was fed via line 4 to the reactor 5, into which gaseous ammonia (50 m$^3$ (S.T.P.)/hour) was introduced via line 6. Some of the ammonia required in reactor 5 was passed from the vapor/liquid separator 9 via line 10 to the compressor 11 and fed into the ammonia supply. Excess ammonia, the water formed during the reaction and the accompanying organic products, such as nicotinamide, nicotinic acid, pyridine and nicotinic acid nitrile, were continuously removed from reactor 5 via line 7. After this stream had been cooled in the heat exchanger 8, the mixture was introduced into the liquid/vapor separator 9. Gaseous ammonia was recycled to the reactor via line 10, and te aqueous solution from the separator was removed via line 12.

The crude nicotinamide melt obtained in the reactor was introduced via line 13 into the top section of a rectification column 14. 100 kg/hour of pure, molten nicotinamide were obtained in a lateral take-off at the bottom of the column via line 15. A circulation stream consisting of 40% by weight of nicotinic acid, 60% by weight of nicotinamide and a little nicotinic acid nitrile was isolated at the top of the column and recycled to the mixing tank 1 via line 3.

We claim:

1. In a process for the preparation of nicotinamide by amidation of nicotinic acid, the improvement which comprises:

reacting a solution of nicotinic acid in nicotinamide, with a nicotinic acid content of 50 to 80% by weight based on the solution, in a first stage with an excess of ammonia at from 190° to 240° C., while removing the water of reaction at the same time by distillation;

subjecting the resulting solution, which is a crude mixture of nicotinic acid and predominantly nicotinamide, in a second stage to fractional distillation in a column under vacuum, removing a pure nicotinamide at the bottom of the column and removing a mixture of nicotinic acid and nicotinamide with a lower nicotinamide content than the feed at the top of the column; and recycling said nicotinic acid/nicotinamide mixture obtained in the second stage to the first stage while replenishing the recycled mixture with fresh nicotinic acid.

2. A process as claimed in claim 1, wherein the amidation is carried out continuously at from 200° to 220° C.

3. A process as claimed in claim 1, wherein a mixture of nicotinic acid and nicotinamide with an amide content of from 60 to 95% by weight is removed from the first stage and transferred to the distillation stage.

4. A process as claimed in claim 1, wherein the distillation in the 2nd stage is carried out continuously and a mixture of approximately equal amounts of nicotinic acid and nicotinamide is removed at the top.

5. A process as claimed in claim 1 wherein the ammonia is used in a molar excess of from 0.5 to 4 times the molar amount required for the conversion.

6. A process as claimed in claim 1 wherein the ammonia is used in a molar excess of from 1 to 2.5 times the molar amount required for the conversion.

7. A process as claimed in claim 1 wherein the crude mixture transferred as a solution from the first amidation stage to the second distillation stage contains from about 60 to 95% by weight of nicotinamide, about 4 to 39% by weight of nicotinic acid, about 0.1 to 2% by weight of nicotinic acid nitrile and trace amounts of pyridine, water and ammonia.

* * * * *